United States Patent [19]

Weitz et al.

[11] Patent Number: 5,688,507
[45] Date of Patent: Nov. 18, 1997

[54] METHODS AND COMPOSITIONS FOR INHIBITING THROMBOGENESIS

[75] Inventors: Jeffrey I. Weitz, Ancaster; Jack Hirsh, Hamilton, both of Canada

[73] Assignee: Hamilton Civic Hospitals Research Development, Inc., Ontario, Canada

[21] Appl. No.: 559,256

[22] Filed: Nov. 13, 1995

Related U.S. Application Data

[63] Continuation of Ser. No. 175,211, Dec. 27, 1993, abandoned.

[51] Int. Cl.$^6$ .................................................. A61K 39/395
[52] U.S. Cl. .................................. 424/184.1; 424/130.1; 424/278.1
[58] Field of Search ........................... 424/184.1, 130.1, 424/278.1

[56] References Cited

U.S. PATENT DOCUMENTS

| | | |
|---|---|---|
| 5,023,236 | 6/1991 | Edgington et al. . |
| 5,189,019 | 2/1993 | Palladino et al. . |
| 5,196,404 | 3/1993 | Maraganore et al. ............... 514/13 |
| 5,223,427 | 6/1993 | Edgington et al. . |
| 5,239,058 | 8/1993 | Vlasuk et al. . |
| 5,240,913 | 8/1993 | Maraganore et al. ............... 514/13 |

FOREIGN PATENT DOCUMENTS

| | | |
|---|---|---|
| 0347959 | 5/1989 | European Pat. Off. . |
| WO 90/00178 | 1/1990 | WIPO . |
| 9102750 | 3/1991 | WIPO . |
| WO 92/01464 | 2/1992 | WIPO . |
| WO 92/04378 | 3/1992 | WIPO . |
| WO 92/06711 | 4/1992 | WIPO . |
| WO 92/10575 | 6/1992 | WIPO . |
| 9213952 | 8/1992 | WIPO . |
| WO 93/09803 | 5/1993 | WIPO . |

OTHER PUBLICATIONS

Weitz et al. 1990. Clot-bound Thrombin is Protected from Inhibition by Heparin . . . J. Clin. Invest. 86:385–91.
Liu et al. 1979. The Binding of Thrombin by Fibrin. JBC. 254(20):10421–10425.
Liu, Le-Wen et al. "Occupancy of Anion Binding Exosite 2 on Thrombin Determines $Ca^{2+}$ Dependence of Protein C Activation," (1994) The Journal of Biological Chemistry vol. 269, No. 16, pp. 11807–11812.
Arni, Raghuvir K. et al. "Structure of the non-covalent complex of prothrombin kringle 2 with PPACK-thrombin," (1994) Chemistry and Physics of Lipids 67/88 pp. 59–66.
Arni, Raghuvir K. et al. "Structures of the Noncovalent Complexes of Human and Bovine Prothrombin Fragment 2 with Human PPACK-Thrombin," (1993) Biochemistry 32, pp. 4727–4737.
Rubens et al., The Effect of Antithrombin III-Independent Thrombin Inhibitors and Heparin on Fibrin Accretion . . . , Thrombosis & Hemostasis, vol. 69, No. 2, Feb. 1993, pp. 130–134.

Vali et al., Localization of the Binding Site on Fibrin for the Secondary Binding Site of Thrombin, Biochemistry, vol. 27, 1988, pp. 1956–1963.
Siebenlist et al., The Polymerization and Thrombin–Binding Properties of Des–(Bβ1–42)–Fibrin, Jor. of Biological Chem., vol. 265, No. 30, 1990, pp. 18650–18655.
Colman et al., *Hemostasis and Thrombosis, Basic Principles and Clinical Practice*, 2nd Ed., published by Lippincott Co., 1987, pp. 148–150.
Maraganore et al., Design and Characterization of Hirulogs: A Novel Class of Bivalent Peptide Inhibitors of Thrombin, Biochemistry, vol. 29, 1990, pp. 7095–7101.
Doolittle, Fibrinogen and Fibrin, Scientific American, vol. 245, No. 6, 1981, pp. 92–101.
Walz et al., Amino Acids Sequence of Human Prothrombin Fragments 1 and 2, Proc. Natl. Acad. Sci. of USA, vol. 74, No. 5, May 1977, pp. 1969–1972.
Weitz et al., New Anticoagulant Strategies, Jor. of Lab. and Clinical Medicine, vol. 122, No. 4, Oct. 1993, pp. 364–373.
Stubbs and Bode (1993) Thrombosis Res. 69:1–58.
Hirsh (1993) Circ. vol. 88, No. 4, Part 2, I–C, I–D.
Arni et al. *Biochemistry* (1993) 32:4727–4737. Structures of the Noncovalent Complexes of Human and Bovine Prothrombin Fragment 2 with Human PPACK–Thrombin.
Arnaud et al. *Blood* (1994) 84:1843–1850. An Autoantibody Directed Against Human Thrombin Anion–Binding Exosite in a Patient With Arterial Thrombosis: Effects on Platelets, Endothelial Cells, and Protein C Activation.
Noe et al. *J. Biol. Chem.* (1988) 263:11729–11735. The Use of Sequence–specific Antibodies to Identify a Secondary Binding Site in Thrombin.
Sie et al. *J. Clin. Invest.* (1991) 88:290–296. An Acquired Antithrombin Autoantibody Directed toward the Catalytic Center of the Enzyme.
Wu et al. *J. Biol. Chem.* (1994) 269:3725–3730. Activation–induced Exposure of the Thrombin Anion–binding Exosite.

*Primary Examiner*—Paula K. Hutzell
*Assistant Examiner*—Benet Prickril
*Attorney, Agent, or Firm*—Townsend and Townsend and Crew LLP

[57] ABSTRACT

Thrombus or clot formation and accretion are inhibited by administering thrombin-displacing substances to a patient. The thrombin-displacing substances comprise either thrombin analogs which bind to the thrombin-binding site on fibrin or fibrin analogs which bind to a fibrin-binding site on thrombin. By displacing the thrombin from clot or thrombus, the thrombin is released into circulation where it is inactivated by endogenous anti-proteinases. The fibrin analogs which bind to the fibrin-binding site on thrombin may be linked to a second binding moiety which binds to and/or inactivates the catalytic site on thrombin to further inhibit thrombosis.

4 Claims, 6 Drawing Sheets

METHODS AND COMPOSITIONS FOR INHIBITING THROMBOGENESIS

This is a continuation of application Ser. No. 08/175,211, filed Dec. 27, 1993, now abandoned.

BACKGROUND OF THE INVENTION

1. Field of the Invention

The present invention relates generally to methods and compositions for the treatment of cardiovascular disease. More particularly, the present invention relates to novel methods and compositions to inhibit thrombus formation and growth by displacing thrombin bound to fibrin in thrombus or clot.

Thrombosis is a pathological manifestation of the clotting cascade in blood vessels. The clotting cascade is a complex biological process which results in the formation of clot or thrombus composed of platelets and fibrin. Thrombosis, together with atherosclerosis, can cause partial or total occlusion of the affected blood vessel, thereby leading to a number of important cardiovascular complications, including unstable angina, acute myocardial infarction (heart attack), cerebral vascular accidents (stroke), pulmonary embolism, deep vein thrombosis, and arterial thrombosis. These diseases are a major cause of disability and mortality in Western societies.

Of particular interest to the present invention, the clotting cascade results in the activation of thrombin, which is a multi-functional serine protease that mediates thrombosis by activating platelets and cleaving fibrinogen to produce fibrin. Thrombin also induces smooth cell proliferation and may thus be involved in proliferative responses, such as graft-induced atherosclerosis and restenosis after angioplasty and atherectomy.

Clot or thrombus which forms as a result of activation of the clotting cascade contains fibrin, platelets, and numerous other blood components. Thrombin is bound to fibrin where it remains active and causes growth of the clot by continued cleavage of fibrinogen and activation of platelets and other blood factors, such as factor V and factor VIII. Because thrombin is critical to thrombus formation, the use of thrombin inhibitors for treating thrombosis and thrombotic complications has long been proposed. A number of at least partially effective inhibitors have been in use for years. For example, heparin can be used as an anticoagulant and antithrombin agent to prevent platelet aggregation and thrombus formation. Heparin, however, has a number of limitations. The doses required are quite unpredictable, and heparin is unable to inactivate clot-bound thrombin, allowing the continued growth of thrombus mediated by thrombin within pre-existing thrombus.

Inactivation of clot-bound thrombin may be achieved with another set of compounds including hirudin and its derivatives. Hirudin is an antithrombin substance extracted from the salivary glands of the leech. Related compounds include hirulog, which is a small analog of hirudin. While these drugs are able to inhibit clot-bound thrombin, the inactivation is reversible so that the inhibitory effect is lost when the drugs are cleared from the blood.

A third class of drugs bind reversibly or irreversibly to the active (catalytic) site of thrombin. One such irreversible active site inhibitor is PPACK (D-phenylalanyl-L-propyl-L-arginyl chloromethyl ketone). Such inhibitors, however, generally lack sufficient specificity for thrombin and thus have questionable safety. Moreover, there is some evidence that total inhibition of thrombin with irreversible active site inhibitors can lead to excessive bleeding.

For these reasons, it is desirable to identify novel methods and compositions for inhibiting thrombogenesis associated with cardiovascular disease. In particular, it would be desirable to provide methods and compositions which are capable of permanently reducing or eliminating fibrin-bound thrombin activity from existing thrombi within the vascular system. Such elimination or reduction of clot-bound thrombin should be essentially irreversible so that clot accretion will not resume after administration of a treating agent is stopped. It would be particularly desirable to develop methods and compositions which are able to inactivate thrombin within the thrombus with an agent that does not directly inhibit clotting, since such agents would not adversely affect bleeding control (hemostasis). Such an agent could be a compound which would displace and release thrombin into blood circulation where it would be inactivated by natural antithrombin components, such as antithrombin III.

2. Description of the Background Art

Hirudin derivatives for blocking the active site of thrombin are described in U.S. Pat. Nos. 5,240,913 and 5,196,404. A bifunctional antithrombotic composition which includes both a glycoprotein IIb/IIIa inhibitory domain and a thrombin inhibitory domain is described in WO 92/10575. Peptide analogs of glycoprotein IIIa for thrombogenesis inhibition are described in WO 90/00178. Inhibitors of factor X and/or Xa are described in U.S. Pat. Nos. 5,239,058 and 5,189,019 and PCT publications WO 93/09803; WO 92/04378; and WO 92/01464. Inhibitors of factors VII and/or VIII are described in U.S. Pat. Nos. 5,223,427 and 5,023,236 and WO 92/06711. Platelet antiadhesives and related antibodies are described in WO 92/08472. Stubbs and Bode (1993) *Thrombosis Research* 69:1–58, is a review article describing the structure and function of thrombin. Hirsh (1993) *Circ.* 88: I-C summarizes a lecture relating to the limitations of heparin and potential advantages of new, anticoagulants as antithrombotics.

SUMMARY OF THE INVENTION

The present invention comprises methods and compositions for displacing thrombin from thrombus by exposing the thrombus to a substance, other than thrombin, which binds to a thrombin-binding site on fibrin or to a fibrin-binding site on thrombin. Binding occurs with sufficient affinity to displace thrombin from the thrombus and to inhibit rebinding of thrombus which may be present in a surrounding aqueous environment, typically blood. The methods will be particularly useful for inhibiting thrombus accretion by removing active thrombin from thrombus to inhibit the clotting cascade at the thrombus, particularly in patients suffering from a cardiovascular disease. In such patients, released thrombin will be inactivated by endogenous thrombin inhibitors present in circulation.

The present invention further comprises pharmaceutical compositions comprising or consisting essentially of the substance which binds to a thrombin-binding site on fibrin or a fibrin-binding site on thrombin with the requisite affinity. Substances which bind to fibrin may be selected from the group consisting of thrombin fragments, thrombin analogs, and antibody and antibody fragments which bind to the thrombin-binding site on fibrin thrombin mimetics, and the like. Such fibrin-binding substances will bind to the thrombin-binding site on fibrin with an affinity of at least $5 \times 10^4$ $M^{-1}$, preferably being at least about $10^5 M^{-1}$, more preferably being at least $5 \times 10^5$, or higher.

Substances which bind to the fibrin-binding site on thrombin may be selected from the group consisting of fibrin fragments, fibrin analogs, soluble $F_2$ from prothrombin and fragments thereof, and antibody and antibody fragments which bind to the fibrin-binding site on thrombin, fibrin mimetics, and the like. Such substances will bind to the fibrin-binding site on thrombin with an affinity of at least $10^7 M^{-1}$, preferably being at least about $10^8 M^{-1}$, or higher.

The present invention still further provides thrombin inhibitors which comprise a hybrid molecule having a first moiety which binds to the fibrin-binding site on thrombin and a second moiety which binds to and/or sterically interferes with a proteolytic (catalytic) site on thrombin, wherein the first and second moieties are spaced-apart by a distance sufficient to permit simultaneous binding of both moieties to their respective binding sites.

The first moiety is selected from the group consisting of fibrin and fragments, fibrin analogs, $F_2$ from prothrombin and fragments thereof, antibody and antibody fragments which bind to the fibrin-binding site on thrombin, and fibrin mimetics, and will have a binding affinity of at least about $10^7 M^{-1}$, preferably being at least about $10^8 M^{-1}$. The second moiety may be any compound, component, or structure which binds to the proteolytic (catalytic) site on thrombin, typically being derived from known thrombin inhibitors, such as PPACK, hirudin, anti-thrombin antibodies, and the like. Alternatively, the second moiety could bind to a site sufficiently near the thrombin catalytic site so that said moiety, when bound, will sterically interfere with the normal catalytic activity, usually by inhibiting binding of fibrinogen. The hybrid molecules may be prepared by conventional chemical synthesis techniques, or in the case of polypeptides, may be prepared recombinantly as fusion proteins. The binding affinity between the second moiety and the proteolytic site will be at least about $10^5 M^{-1}$, preferably being at least about $5 \times 10^5 M^{-1}$. The distance between first and second binding moieties will typically be in the range from about 5 Å to 25 Å, preferably in the range from about 10 Å to 20 Å.

A further understanding of the nature and advantages of the invention will become apparent by reference to the remaining portions of the specification and drawings.

BRIEF DESCRIPTION OF THE DRAWINGS

F denotes fibrin; T denotes thrombin; FS denotes the fibrin-binding site on thrombin; CS denotes the catalytic site on thrombin; and FBS denotes the fibrinogen-binding site on thrombin.

F denotes fibrin; T denotes thrombin; FS denotes the fibrin-binding site on thrombin; CS denotes the catalytic site on thrombin; and FBS denotes the fibrinogen-binding site on thrombin; and FA denotes a fibrin analog.

F denotes fibrin; FS denotes a fibrin-binding site on a thrombin analog; TA denotes a thrombin analog; T denotes thrombin; FS denotes the fibrin-binding site on thrombin; CS denotes the catalytic site on thrombin; and FBS denotes the fibrinogen-binding site on thrombin.

DETAILED DESCRIPTION OF SPECIFIC EMBODIMENTS

The present invention provides methods and compositions for interfering with and disrupting binding between thrombin and fibrin within thrombus and clot, whereby the ability of clot-bound thrombin to catalytically promote further clot accretion is diminished or eliminated. The compositions and methods of the present invention are particularly useful for treating patients suffering from or at risk of suffering from thrombus-related cardiovascular conditions, such as unstable angina, acute myocardial infarction (heart attack), cerebrovascular accidents (stroke), pulmonary embolism, arterial thrombosis, deep vein thrombosis, and the like. The present invention is not limited to such uses, however, and the methods and compositions described herein may find use in other in vitro and in vivo situations whenever it is desirable to inhibit clot or thrombus accretion or promote clot or thrombus solubilization. For example, the compositions of the present invention may be used as an anti-coagulant for inhibiting thrombin-induced clotting in various in vitro studies, assays, and the like.

The present invention is based at least in part on the recognition that the fibrin-binding site on thrombin is distinct from the fibrinogen-binding site. That is, when thrombin is bound to fibrin, as is the case in clot or thrombus matrices, the fibrin-binding site will be occupied while the fibrinogen-binding site remains sterically available to bind fibrinogen and orient the bound fibrinogen for interaction with the thrombin catalytic site which promotes the conversion of fibrinogen to fibrin.

Figure 1:
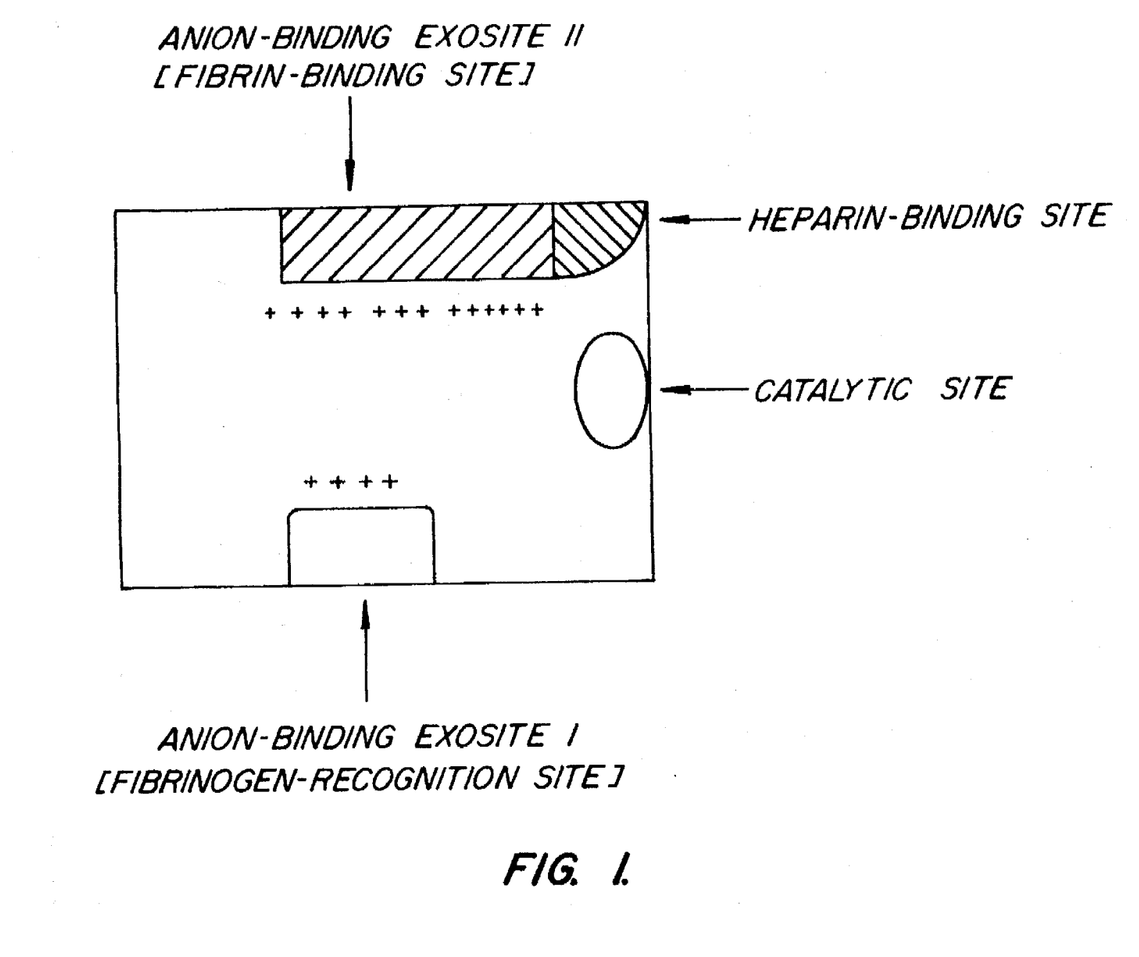
FIG. 1 is a schematic illustration of the thrombin molecule illustrating the relative positions of the fibrin-binding site (anion-binding exosite II), the heparin-binding site, the catalytic site, and the fibrinogen-recognition site (anion-binding exosite I).

Referring to FIG. 1, the relevant binding domains of thrombin will be described. Thrombin is a trypsin-like serine protease which displays a number of activities in the clotting cascade (blood coagulation pathway), including the conversion of soluble fibrinogen into insoluble fibrin, wherein fibrinopeptides A and B are cleaved from the amino-terminal regions of the α- and β-chains of fibrinogen, respectively. As a result of this reaction, thrombin becomes bound to fibrin at the fibrin-binding site (anion-binding exosite II) in the clot or thrombus formed. As the fibrin-binding site is remote from both the fibrinogen-recognition site (anion-binding exosite I) and the catalytic site, the clot-bound or thrombus-bound thrombin remains catalytically active and protected from inactivation from serum anti-proteinases. Thus, the fibrin-bound thrombin in the clot or thrombus remains available to locally amplify coagulation through activation of platelets, factor V, and factor VIII, as well as through the conversion of fibrinogen to fibrin, in order to cause clot growth. In addition, the clot-bound thrombin can activate factor XIII which then cross-links the newly-formed fibrin thereby rendering it less susceptible to lysis.

Referring to FIG. 1 in more detail, thrombin is a globular-elliposoid molecule having an active catalytic site on a surface thereof. The fibrinogen-recognition site (anion-exosite I) is a highly positively charged region which interacts with fibrinogen as well as with thrombomodulin, and which is the site of binding by hirudin and hirulog, as discussed previously. Binding to the anion-binding exosite I is an important step in orienting substrates relative to the catalytic site in order to achieve efficient proteolytic hydrolysis of the substrates, including fibrinogen and thrombomodulin.

The inventors herein have recognized that a second positively charged binding site on thrombin, designated anion-binding exosite II, is involved in the binding of thrombin to fibrin in clot and thrombus. The anion-binding exosite II is located near to or overlapping with the heparin-binding site on thrombin and is centered around the side chains of the Arg 93, Arg 126, Lys 236, and Lys 240 residues on the thrombin molecule and extends to the left to encompass the side chains of the Arg 97, Arg 101, Arg 165, Lys 161, Arg 173, Arg 175, Arg 233, and Lys 235 residues. In addition to heparin, the $F_2$ fragment of prothrombin also binds to this region, and the anion-binding exosite II is masked in prothrombin, meizothrombin and prethrombin I.

The present invention relies on disrupting or interfering with binding between the fibrin-binding site on the thrombin and/or the thrombin-binding site on fibrin in order to release thrombin from thrombus or clot into a surrounding aqueous environment, usually into blood in the vascular environment. While fibrin-bound thrombin in thrombus or clot is protected from inactivation by heparin and endogenous anti-proteinases, thrombin released from clot or thrombus will become susceptible to inactivation from endogenous anti-proteinases and/or appropriate drug therapies. The methods and compositions of the present invention can provide for complete or near-complete release and displacement of clot-bound or thrombus-bound thrombin whereby thrombin-mediated amplification of coagulation is substantially inhibited or prevented. Usually, at least about 95% inhibition of thrombus-bound thrombin may be achieved, preferably being at least about 99% inhibition, and more preferably being at least about 100% inhibition. By "inhibition," it is meant that the thrombin activity is irreversibly inactivated so that the thrombin molecule cannot promote thrombus or clot formation or accretion.

Figure 2A:
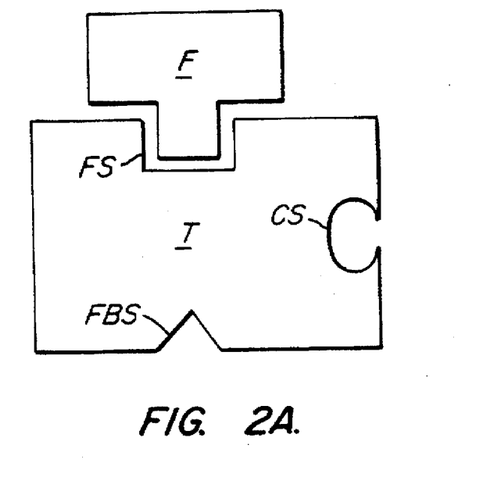
FIG. 2A illustrates the thrombin molecule bound to fibrin, as would be the case in formed thrombus or clot. The following abbreviations are used.
Figure 2B:
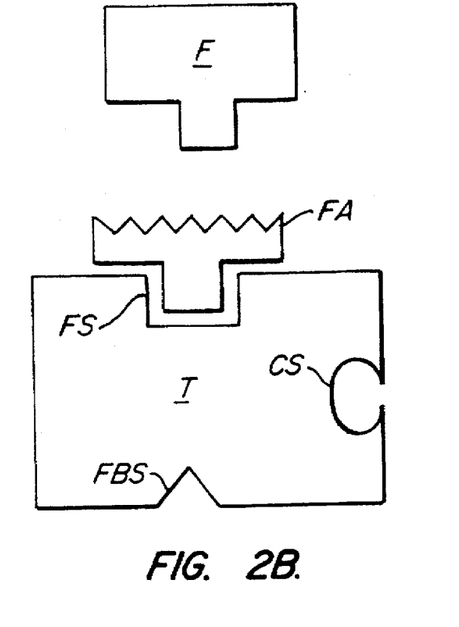
FIG. 2B illustrates the mechanism underlying the present invention where a fibrin analog or other mimetic compound (such as soluble $F_2$ from prothrombin of fragments thereof) has displaced fibrin at the fibrin-binding site on thrombin to release thrombin from the clot. The following abbreviations are used.

Referring now to FIGS. 2A and 2B, a first mechanism for displacing thrombin from fibrin in clot or thrombus will be described. In clot and thrombus, thrombin T is bound to fibrin F with the fibrinogen binding site FBS and the catalytic (proteolytic) site CS remaining sterically available (FIG. 2A) for promoting blood coagulation which results in thrombus and clot accretion, as described previously. In order to displace thrombin from the thrombus, a fibrin analog FA is introduced to the thrombus (typically via introduction into patient circulation) to bind to the fibrin binding site FS on thrombin T, as illustrated in FIG. 2B. The fibrin analog may be any substance that will bind to the fibrin binding site FS on thrombin in place of clot-fibrin in order to release the thrombin from thrombus into circulation.

Suitable fibrin analogs include fibrin fragments, modified fibrin polypeptides, soluble $F_2$ from prothrombin and fragments thereof, fibrin mimetics (small molecules designed to bind to the fibrin-binding site on thrombin in preference to native fibrin), antibodies and antibody fragments specific for the fibrin-binding site on thrombin, or any other substance capable of entering the thrombus/clot matrix and disrupting binding between clot-bound fibrin and thrombin in order to release thrombin from the thrombus.

The fibrin analog will have a binding affinity for fibrin-binding site on thrombin which is usually greater than the native binding affinity between fibrin and thrombin in thrombus. The native binding affinity is about $5 \times 10^{-5} M^{-1}$, and the binding affinity of the fibrin analog will usually be at least $10^7 M^{-1}$, preferably being at least $10^8 M^{-1}$, or higher. Generally, fibrin analogs, will be utilized at lower concentrations than thrombin analogs since there are fewer thrombin molecules to block. To maintain the desired blocking and inhibition, it is desirable to utilize fibrin analogs having a higher binding affinity than the native affinity between thrombin and fibrin in clot.

In addition to such threshold binding affinity, the fibrin analogs should display binding kinetics which permit displacement of fibrin from the thrombus-bound thrombin in a rapid manner. Additionally, suitable fibrin analogs will have relatively long half-life in circulation, preferably being at least as great as the half-life of thrombin released from the thrombus, preferably being longer than that of thrombin. It will be appreciated, however, that the only essential requirement for fibrin analogs according to the present invention is the ability to displace thrombus-bound thrombin and release said thrombin into circulation where it will be inactivated by endogenous anti-proteinases.

In particular, fibrin analogs may be peptidic, e.g., comprising or consisting essentially of the thrombin-binding site on fibrin, the soluble $F_2$ fragment of prothrombin, or portions or fragments thereof. The thrombin-binding site on fibrin is located on the central E-domain of fibrin, as described in Mosesson (1990) J. Lab. Clin. Med. 116:8–17; Vali et al. (1988) Biochemistry 27:1956–1963; and Kaminski and McDonaugh (1987) Biochem. J. 242:881–887. Such peptidic analogs and $F_2$ fragments can be prepared by conventional solid phase synthesis or recombinant techniques, as are well described in the art. Suitable solid phase synthesis techniques are based on the sequential addition of amino acids to a growing chain on a solid-phase substrate, as first described in Merrifield (1963) J. Am. Chem. Soc. 85:2149–2156. Commercial systems for automated solid-phase synthesis are now widely available from suppliers, such as Applied Biosystems, Inc., Foster City, Calif. Recombinant polypeptide production techniques are widely described in the technical and scientific literature. See, for example, *Molecular Cloning: A Laboratory Manual*, Sambrook et al., Eds., Cold Spring Harbor Laboratory Press, Cold Spring Harbor, N.Y. (1989), Vols. 1–3.

The substance which serves as the fibrin analog may also be an antibody or antibody fragment which binds to the fibrin-binding site on thrombin, or a small molecule mimetic (typically having a molecule weight below 3 kD, usually below 2 kD, and often below 1 kD) which displays similar or enhanced binding characteristics relative to intact fibrin. Such antibodies may be prepared by employing thrombin, or a thrombin fragment comprising the fibrin-binding site, as an immunogen in conventional techniques for preparing polyclonal or monoclonal antibodies. Such techniques are well described in the scientific and patent literature. See, for example, *Antibodies: A Laboratory Manual*, Harlow and Lane, Eds., Cold Spring Harbor Laboratory Press, Cold Spring Harbor, N.Y., (1988). The preparation of small molecule mimetics is further described below.

Figure 2C:
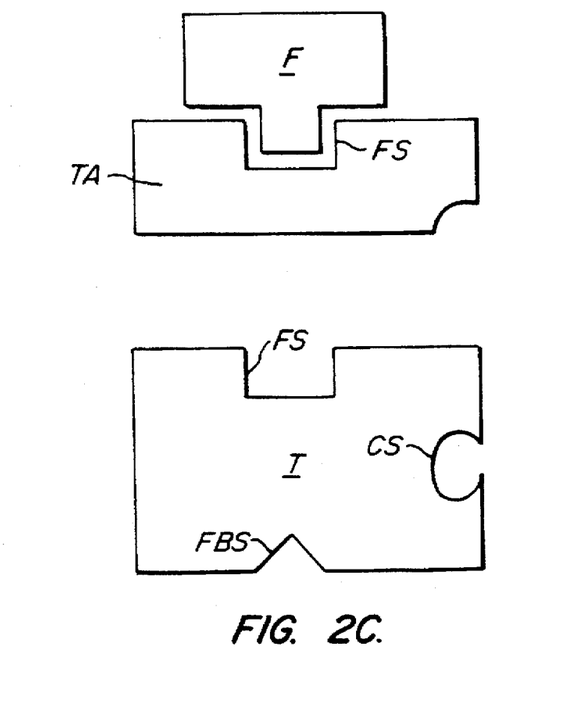
FIG. 2C illustrates an alternative mechanism underlying the present invention where a thrombin analog or other mimetic compound has been introduced to bind to the thrombin-binding site on fibrin and to thereby displace previously bound thrombin from the clot or thrombus. The following abbreviations are used.

A second mechanism for thrombin displacement according to the present invention is illustrated in FIG. 2C, where a thrombin analog TA is introduced to thrombus or clot to disrupt binding between thrombin T and fibrin F. The thrombin analog TA will possess a fibrin-binding site FS having an affinity which is at least equal to, and preferably greater than, the native binding affinity between thrombin and fibrin as described above. Thus, the thrombin analog will preferably bind to fibrin with affinity of at least $5 \times 10^4 M^{-1}$, preferably being at least $10^5 M^{-1}$, and more preferably being at least $5 \times 10^5 M^{-1}$. The thrombin analogs may possess a lower binding affinity than the fibrin analogs since the thrombin analogs will be used at higher concentrations (to block the excess fibrin that may be present). Principles of mass action dictate that equivalent displacement will be achieved under both circumstances. The thrombin analog will also possess adequate binding kinetics and serum survivability, as described above for the fibrin analog.

Suitable thrombin analogs include thrombin fragments comprising the fibrin-binding site, as described above. Thrombin mimetics will also be useful for thrombin displacement, where such mimetics are small molecules designed to mimic the fibrin-binding site. Additionally, the thrombin analogs may comprise the $F_2$ fragments from prothrombin, as well as analogs and mimetics thereof, as well as comprising antibodies and antibody fragments which are capable of binding to the thrombin-binding site on fibrin. The preparation of polypeptide analogs and antibodies and antibody fragments may be carried out by the conventional techniques described above in connection with preparation of the fibrin analogs.

Small molecule mimetics of both the fibrin analogs and thrombin analogs can be achieved through the use of techniques known to those working in the area of drug design. Such methods include, but are not limited to, self-consistent field (SEF) analysis, configuration interaction (CI) analysis, and normal mode dynamics computer programs, all of which are now readily available. See, Rein et al., *Computer-Assisted Modeling of Receptor-Ligand Interactions*, Alan Liss, New York (1989) and Navia and Marcko, "Use of Structural Information in Drug Design," in *Current Opinion in Structural Biology*, Vol. 2, No. 2, pages 202–210, 1992. The preparation of compounds identified by these techniques will depend on their structure and other characteristics and may normally be achieved by standard chemical synthesis methods, as described in available texts, such as Furniss et al., *Vogel's Textbook of Practical Organic Chemistry.*, John Wiley & Sons, New York 1992 and Larock, *Comprehensive Organic Transformations*, VCH Publishers, Inc., New York 1989.

Compositions according to the present invention will also include multivalent, usually bivalent, thrombin inhibitors comprising a hybrid molecule having a first moiety which binds to a fibrin-binding site on thrombin and a second moiety which binds to (or near) the catalytic (proteolytic) site on thrombin. The first moiety may comprise any of the thrombin-binding substances (i.e., fibrin analogs) described above, while the second moiety will be selected to bind to and sterically hinder and/or inactivate the catalytic site on thrombin. Suitable second moieties include substances which are capable of binding to and/or sterically hindering the catalytic site, usually binding to the site with an affinity of at least $10^5 M^{-1}$, preferably being at least $5 \times 10^5 M^{-1}$. Exemplary second moieties include PPACK ([D]Phe-Pro-Arg-X), antibodies and antibody fragments which bind at or near the thrombin catalytic site, and other peptides selected or designed to have the requisite binding characteristics. Small molecules (typically below 2 kD and usually below 1 kD) may also be designed to bind to or sufficiently near to the catalytic site to provide the desired inhibition of catalytic activity.

Figure 3:
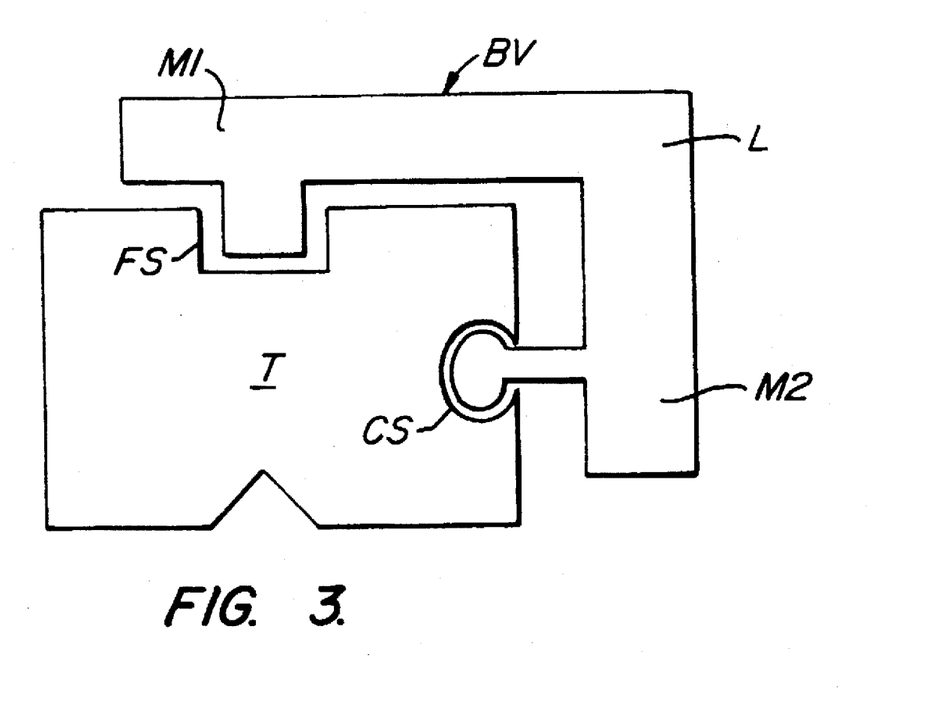
FIG. 3 illustrates a still further embodiment of the present invention where a bivalent molecule including a first moiety capable of binding to the fibrin-binding site on thrombin and a second moiety capable of binding to the proteolytic (catalytic) site on thrombin is used to both displace thrombin from clot and inactivate the displaced thrombin.

As illustrated in FIG. 3, a bivalent molecule BV according to the present invention comprises a first moiety M1 and a second moiety M2 joined by a linking region L. The linking region or group is selected to provide the necessary covalent bridge between the first binding moiety and the second binding moiety. Frequently, the linking region will be derived from a heterobifunctional compound having a reactive group at one end which is capable of binding to the first binding moiety and a second reactive group which is capable of binding to the second binding moiety. Alternatively, the linking region may be synthesized together with either the first binding moiety, the second binding moiety, or both, and then will include only a single reactive functionality for covalent binding therebetween.

The nature of the linking region is not critical, but it should provide a sufficient spacing and flexibility between the two binding moieties so that the first binding moiety M1 may bind to the fibrin-binding site FS on thrombin while the second binding moiety M2 binds to (or sufficiently near to sterically hinder activity of) the catalytic site, as illustrated. The length of the linking region will usually between about 5 Å and 25 Å, preferably between about 10 Å and 20 Å. The linking region should be resistant to degradation when administered to a patient as part of a therapy according to the present invention and should further not contribute to non-specific adhesion of the hybrid molecule, i.e. adhesion or binding to other than the fibrin-binding site and the catalytic site on thrombin. It will be appreciated that the hybrid molecules should also display no or minimum immunogenicity so that the drugs they comprise may be administered to a patient over an extended period of time.

In addition to the linking of moieties through the use of heterobifunctional linking compounds, it will be possible to prepare polypeptide bivalent molecules via conventional recombinant techniques. In particular, the preparation of fusion proteins where the first and second moietites are represented by different genes and/or gene fragments joined together in proper reading frame with a suitable promoter is possible. Such methods are described in detail in Sambrook et al., supra.

The fibrinogen analogs, thrombin analogs, and multivalent molecules, of the present invention will be incorporated as components in pharmaceutical compositions useful to treat the cardiovascular conditions described above. Such compositions will also be useful in conjunction with conventional thrombolytic treatments, e.g., the administration of tissue plasminogen activator (tPA), streptokinase, and the like, as well as with intravascular intervention, such as angioplasty, atherectomy, and the like.

Suitable pharmaceutical compositions will contain a therapeutic amount of the thrombin-displacing substance of the present invention present in a pharmaceutically acceptable carrier. By a "therapeutic amount" it is meant that sufficient thrombin-displacing substance will be present in order to promote thrombin dissolution and/or inhibit thrombus accretion when treating a thrombus-related cardiovascular condition, such as those described above. Typically, the thrombin-displacing substance will be present in a pharmaceutical composition at a concentration from about 0.01 μg per dose to 10 mg per dose, usually being in the range from about 1 μm per dose to 1 mg per dose. Daily dosages may also vary widely, depending on the activity of the particular thrombin-displacing substance, usually being between about 1 μg per kg of body weight to about 10 mg per kg of body weight per day, usually being from about 10 μg per kg of body weight to about 1 mg per kg of body weight per day.

The pharmaceutically acceptable carrier can be any compatible, non-toxic substance suitable to deliver the thrombin-displacing substance to the patient. Sterile water, alcohol, fats, waxes, and inert solids, may be used as the carrier. Pharmaceutically acceptable adjuvants, buffering agents, dispersing agents, and the like, may also be incorporated into the pharmaceutical compositions. Such compositions will be suitable for oral, nasal, respiratory, or parenteral administration, preferably being suitable for parenteral administration, i.e., subcutaneous, vascular, and intravenous administration. It may also be possible to deliver the thrombin-displacing substances of the present invention via transdermal administration.

The following examples are offered by way of illustration, not by way of limitation.

EXPERIMENTAL

To examine the ability of various agents to displace thrombin from fibrin, a solid-phase system was developed wherein fibrin was immobilized on the surface of a microtiter plate well. Radiolabeled thrombin was then bound to the fibrin-coated surface, and after washing, the ability of various agents to displace the bound thrombin was evaluated. In this model, the binding of thrombin to immobilized ovalbumin serves as an index of nonspecific binding. The details of the model are as follows: after adding 100 μl of fibrinogen or ovalbumin (each at a concentration of 1 mg/ml) to the wells of microtiter plate, the plates were incubated for 18 hours at 4° C. The wells were then washed three times with 250 μl aliquots of phosphate buffered saline, pH 7.4, containing 0.1% ovalbumin and 6 mg/ml PEG 8,000 (POP buffer). Based on preliminary studies using radiolabeled fibrinogen or ovalbumin, each well bound 1.3±0.2 μg of fibrinogen, or 1.0±0.1 μg of ovalbumin. The immobilized fibrinogen was converted to fibrin I (desAA fibrin) by adding 100 μl of reptilase diluted 1:10,000 in POP buffer. The reptilase was incubated with the fibrinogen for 60 min at 37° C., and the wells were washed three times with 250 μl of POP buffer. The reptilase completely converted the immobilized fibrinogen to fibrin I because quantitative amounts of fibrinopeptide A (2 mol fibrinopeptide A/mol of bound fibrinogen) was recovered in the supernatant buffer.

Figure 4:
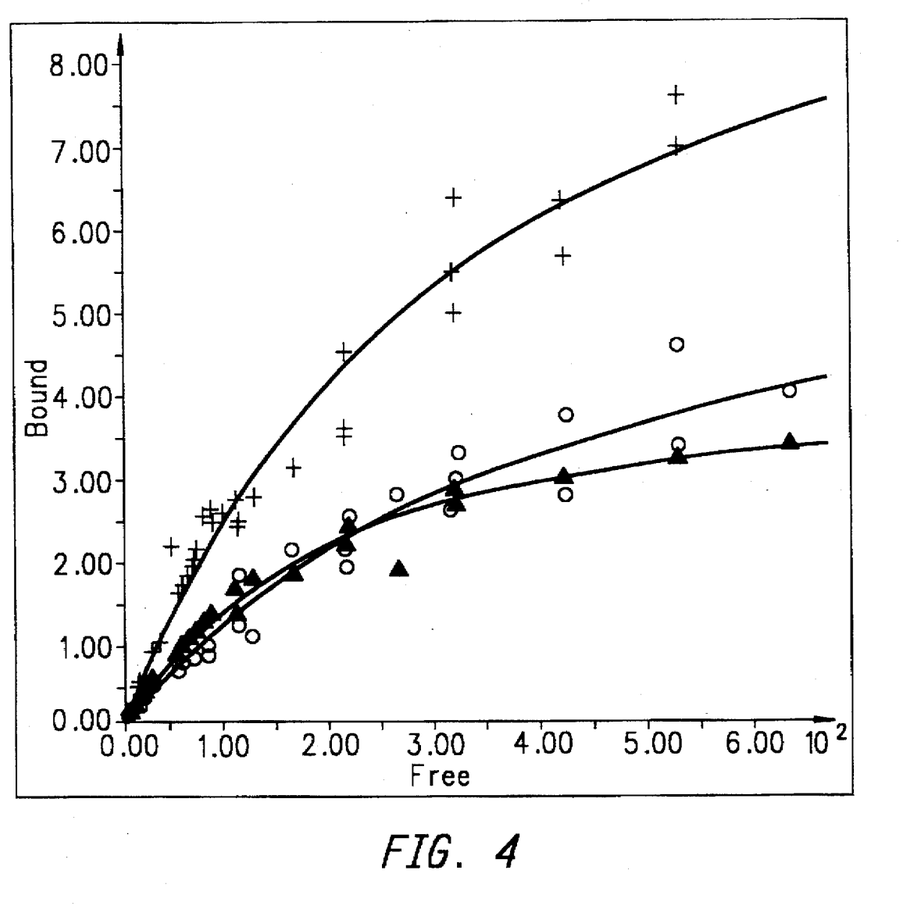
FIG. 4 is a plot of experimental results showing specific binding of thrombin to fibrin-coated wells by subtracting the amount of non-specific binding to ovalbumin-coated wells.

Increasing concentrations of $^{125}$I-thrombin were incubated for 2 h at 37° C. with the fibrin- or ovalbumin-coated wells. Based on the results of other studies, this incubation time ensures maximal thrombin binding (data not shown). At the end of the incubation period, the wells were washed three times and then counted to determine the concentration of thrombin bound to the fibrin-coated (+) or ovalbumin-coated (○) wells (FIG. 4). To calculate the specific binding (Δ) the amount of thrombin bound to the ovalbumin-coated wells was subtracted from that bound to the fibrin-coated wells. It was found that thrombin binds to fibrin in a saturable manner. The binding of PPACK-thrombin (described below) is virtually identical to that of α-thrombin consistent with the concept that thrombin binding to fibrin involves a site distinct from the catalytic center. Thrombin binding to the ovalbumin-coated wells serves as a suitable control for these studies because the amount of labeled thrombin that binds to ovalbumin is equivalent to that which binds to the fibrin-coated wells when labeled thrombin is added in the presence of a 500-fold molar excess of unlabeled thrombin.

Using this experimental system, the ability of active-site-blocked thrombin to displace radiolabeled thrombin from the fibrin-coated surface was examined. Active-site-blocked thrombin was prepared by incubating β-thrombin with a 5-fold molar excess of D-Phe-Pro-ArgCH$_2$Cl (PPACK) for 30 min at 37° C. The thrombin was then dialyzed extensively to remove free PPACK. This procedure results in complete inactivation of thrombin because the active-site-blocked material has no amidolytic activity against a chromogenic substrate for thrombin. In addition, free PPACK also is removed because the active-site-blocked thrombin does not inhibit the amidolytic activity of enzymatically active thrombin.

Figure 5:
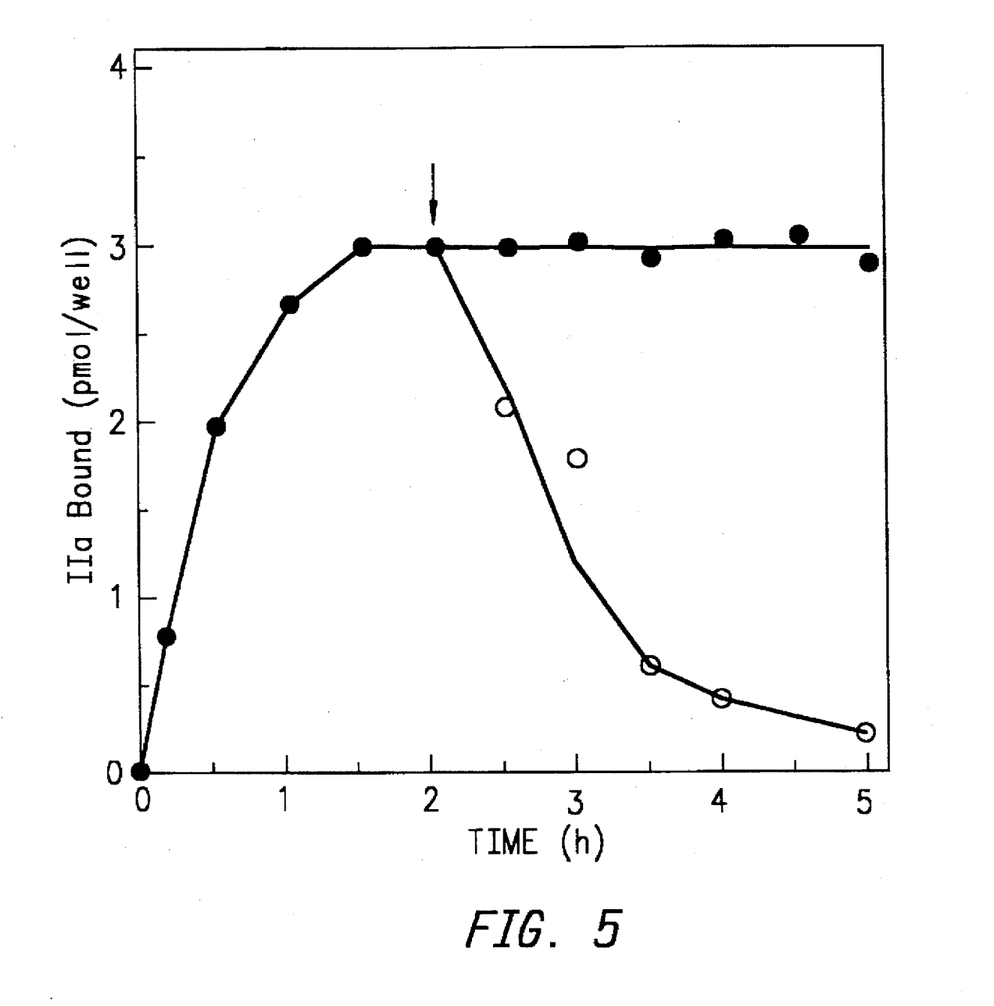
FIG. 5 is an experimental plot of the ability of active-site-blocked PPACK-thrombin to displace labelled thrombin from fibrin-coated wells over time.

To examine the ability of active-site-blocked PPACK-thrombin to displace labeled thrombin from fibrin-coated wells, $^{125}$I-labeled thrombin (5 nmol/well) was incubated with fibrin- or ovalbumin-coated wells for 2 h at 37° C. to ensure maximum binding. At intervals, the wells were washed to remove nonspecifically bound thrombin, and the amount of bound thrombin (FIG. 5,●) was then quantified by counting the radioactivity. At 2 h, a 500-fold molar excess of active-site-blocked PPACK-thrombin (2.5 μmol/well) was added to some of the wells, and the extent of $^{125}$I-labeled thrombin displacement from the fibrin- or ovalbumin-coated wells was monitored over an additional 3 hour period (○). As controls for these experiments, an equivalent volume of buffer was added to other wells in place of the active-site-blocked PPACK-thrombin. At 30-minute intervals, the amount of bound $^{125}$I-labeled thrombin was determined in test and control wells by washing the walls three times and then counting the radioactivity. The specific binding of labeled thrombin to fibrin-coated wells in the presence or absence of active-site-blocked PPACK-thrombin was calculated by subtracting the amount of labeled thrombin bound to ovalbumin-coated wells from that bound to fibrin-coated wells. As illustrated in FIG. 5, labeled thrombin is almost completely displaced from the fibrin-coated surface after the addition of active-site-blocked PPACK thrombin (indicated by the arrow).

Figure 6:
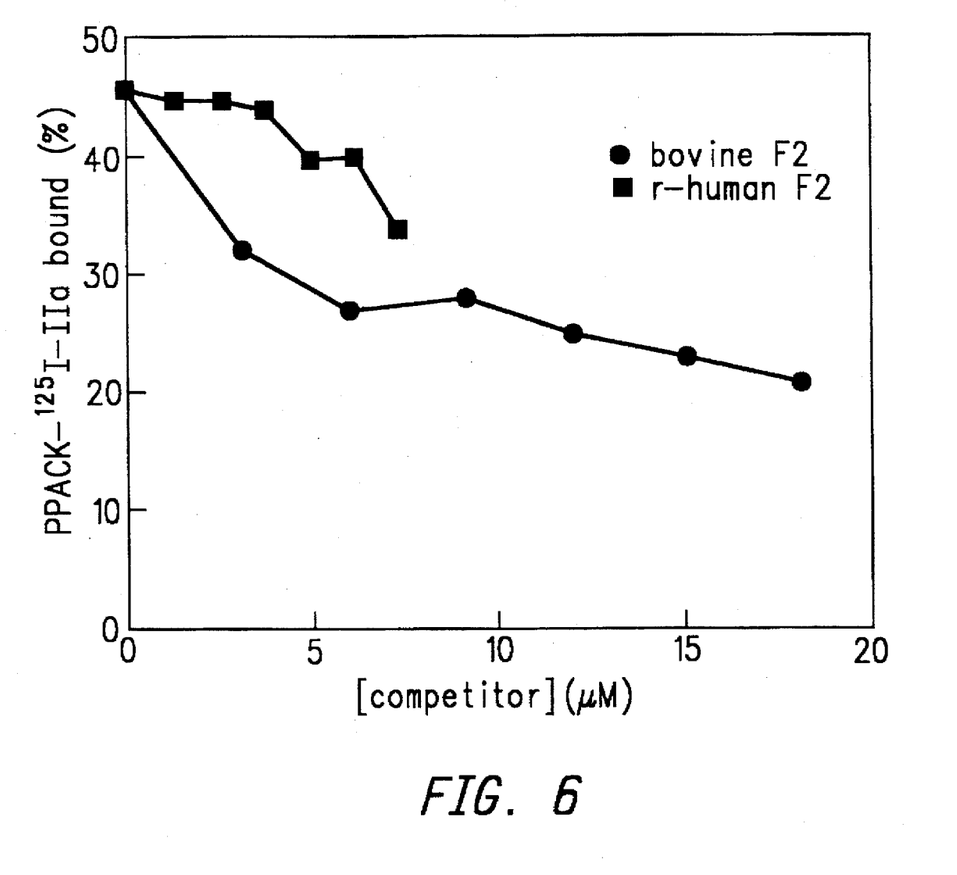
FIG. 6 is an experimental plot showing the ability of prothrombin fragment 2 ($F_2$) to compete with thrombin for binding to fibrin clots.

Prothrombin fragment 2 (F$_2$) was tested to determine its ability to compete with thrombin for binding to fibrin clots. The F$_2$ fragment was selected because the kringle structure within the F$_2$ domain interacts with the heparin-binding site on thrombin (also known as exosite II) thereby interfering with heparin binding to the enzyme. Since we hypothesize that the fibrin-binding domain on thrombin is close to or overlaps the heparin-binding domain, F$_2$ interaction with this region of thrombin should not only prevent heparin binding but should also block fibrin binding. To test this possibility, fibrinogen was clotted with labeled thrombin in the absence or presence of increasing concentrations of bovine or recombinant human F$_2$ fragment. Fibrinogen (2 μM) was incubated with a mixture of 12 nM α-thrombin and 100 nM active-site blocked, $^{125}$I-labelled thrombin in the absence or presence of varying concentrations of bovine (FIG. 6;●) or recombinant human F$_2$ (■). The resultant fibrin clot was then pelleted by centrifugation, the supernatant was collected, and the concentration of active-siteblocked thrombin was determined by counting the radioactivity. As illustrated in FIG. 6, $F_2$ competes with thrombin for fibrin binding in a concentration-dependent fashion. These findings indicate that $F_2$ interacts with the fibrin-binding domain on thrombin and support the concept that the fibrin-binding and heparin-binding domains on thrombin are closely related. In addition, these results indicate that $F_2$ or a fragment thereof may be useful compounds to displace thrombin from fibrin.

Although the foregoing invention has been described in some detail by way of illustration and example, for purposes of clarity of understanding, it will be obvious that certain changes and modifications may be practiced within the scope of the appended claims.

What is claimed is:

1. A method for displacing thrombin bound to fibrin in thrombus, said method comprising exposing the thrombus to a soluble $F_2$ fragment from prothrombin in an aqueous environment, which soluble $F_2$ fragment binds to a fibrin-binding site on thrombin with sufficient affinity to displace thrombin from the thrombus and inhibit thrombin in the aqueous environment from binding to fibrin in the thrombus.

2. A method as in claim 1, wherein the affinity is at least $10^7 M^{-1}$.

3. A method for inhibiting thrombus accretion, said method comprising exposing the thrombus to a soluble $F_2$ fragment from prothrombin which binds to a fibrin-binding site on thrombin with sufficient affinity to displace thrombin from the thrombus.

4. A method as in claim 3, wherein the affinity is at least $10^7 M^{-1}$.

* * * * *